United States Patent
Stelzl (10) Patent No.: US 8,233,697 B2
(45) Date of Patent: Jul. 31, 2012

(54) METHOD AND DEVICE FOR GENERATING DIGITAL STILL PICTURES OF WAFER-SHAPED ELEMENTS DURING A PRODUCTION PROCESS

(75) Inventor: Michael Stelzl, Mainz (DE)

(73) Assignee: Schott AG, Mainz (DE)

( * ) Notice: Subject to any disclaimer, the term of this patent is extended or adjusted under 35 U.S.C. 154(b) by 533 days.

(21) Appl. No.: 12/557,050

(22) Filed: Sep. 10, 2009

(65) Prior Publication Data
US 2010/0061621 A1    Mar. 11, 2010

(30) Foreign Application Priority Data
Sep. 11, 2008  (DE) .......................... 10 2008 046 900

(51) Int. Cl.
*G06K 9/00* (2006.01)
(52) U.S. Cl. ......................... 382/145; 382/147; 382/149
(58) Field of Classification Search .................. 382/145, 382/147, 149
See application file for complete search history.

(56) References Cited

U.S. PATENT DOCUMENTS
2009/0128648 A1 * 5/2009 Ikeda et al. ................ 348/222.1

FOREIGN PATENT DOCUMENTS
DE     101 40 741    2/2003
DE     103 45 581    4/2004

* cited by examiner

*Primary Examiner* — Roy M Punnoose
(74) *Attorney, Agent, or Firm* — Michael J. Striker (57) ABSTRACT

A method and device generate digital still pictures of wafer-shaped elements, such as wafers or solar cells, which are transported in series on a conveyor belt during a production process. The device has a camera taking pictures of the wafer-shaped elements in sections step-by-step, in particular continuously taking digital pictures line-by-line (linear scanning) transverse to the transport direction, and then sampling the recorded image data. The device also includes a hardware-based image data processing unit, e.g. FPGA, for detecting edges of the wafer-shaped elements that indicate a beginning or an end of each of the wafer-shaped elements. The edge detection is for controlling the generation of the digital still pictures for visual inspection to find defective areas of the elements.

22 Claims, 7 Drawing Sheets

METHOD AND DEVICE FOR GENERATING DIGITAL STILL PICTURES OF WAFER-SHAPED ELEMENTS DURING A PRODUCTION PROCESS

CROSS-REFERENCE

The present application claims priority of German Patent Application No. 10 2008 046 900.9, filed on Sep. 11, 2008, under 35 U.S.C. 119 (a) to (d), the entire content of which is hereby incorporated by explicit reference thereto.

BACKGROUND OF THE INVENTION

1. The Field of the Invention

The invention relates to a method for generating digital still pictures of wafer-shaped elements in a production process and relates to a device for executing this method. In particular but not exclusively the invention is applicable to processes for producing photovoltaic or solar cells from wafer-shaped elements which are formed as semiconductor slices or wafers.

2. Description of the Related Art

When manufacturing solar cells the single semiconductor slices or wafers are transported on a conveyor belt, inter alia, for the purposes of optical quality control. Usually this optical quality control or inspection is performed with the assistance of digital image data processing. The purpose is to find out if there are defective areas or spots on the solar cell or wafer. Since the wafers are arranged to one another on the conveyor belt, it is necessary to identify each single wafer separately. Usually sensors are used for it, namely so-called initiators, such as light barriers, ultrasonic sensors, capacitive sensors, mechanical or pneumatic sensors, etc.

Since the wafers are transported on the conveyor belt one after another it is necessary to clearly identify each wafer. For this purpose it is known to use at least one sensor or initiator which detects the beginning and the end of each wafer on the basis of the gaps appearing between two sequenced wafers. However it may happen that adjacent wafers are arranged on the conveyor belt very close to each other so that no gap can be detected. Thus the detection by means of initiators or sensors fails so that the succeeding image data processing for the optical quality inspection is hindered. In particular it can become very complicated or even impossible to make still pictures of the wafers or the solar cells. Thus no corresponding digital single pictures can be extracted which are needed decide whether to sort out the products on the basis of their quality characteristics.

DE 103 45 581 A1 discloses a method of detecting objects being transported on a conveyor belt by taking pictures with the help of a line scan camera. The objects are automobile parts, such as car doors, having edges and holes to be detected for mounting and assembly in a car production process.

DE 103 45 581 A1 discloses a method of detecting objects being transported on a conveyor belt by taking pictures with the help of a line scan camera. The objects are automobile parts, such as car doors, having bore-holes to be detected and measures within a car production process. Thus the method performs a partial scan of a small detailed part of each object, such as a specific bore-hole. It is not described to make a full scan of the entire object (e.g. the door) or to detect gaps between the objects which are sequenced on the conveyor belt.

DE 101 40 741 C1 discloses a device and a method being applied to CT equipment (CT: computer tomography) to improve the positioning of image data generated by a rotating data acquisition system (DAS). The DAS is triggered by a trigger signal in dependence of the angular position of the sensor. If the system fails to generate a trigger within a preset time interval a synthetic trigger is generated. The described solution is thus directed to the synchronization by trigger signals, but it does not describe how to generate digital still pictures of elements or objects transported on a conveyor belt within a production process.

SUMMARY OF THE INVENTION

Therefore it is an object of the present invention to provide a method and a device for generating digital still pictures of wafer-shaped elements in a production process, wherein the above-mentioned drawbacks do not occur, but are overcome in an advantageous manner. In particular a method for generating digital still pictures of the wafer-shaped elements, such as wafers or solar cells, is provided, wherein the method allows a fast and reliable detection of each wafer-shaped element arranged in a series of several wafer-shaped elements which appear on the conveyor belt.

The objective is solved by a method comprising the steps of the independent method claim and by a device comprising the components of the independent device claim.

Accordingly in the method according to the invention digital pictures are continuously taken of the wafer-shaped elements, such as solar cells, which are arranged one after the other in sequence wherein the pictures are taken in sections step-by-step, in particular line-by-line, and crosswise to the direction of the movement of the conveyor belt. Then the obtained image data are evaluated by hardware-based image data processing, in order to detect edges or transitions thereof which indicate the beginning or the end of each of the wafer-shaped elements. Then the generation of digital still pictures from the obtained image data is controlled by the detected edges. Thus the method of the invention achieves a secure and reliable detection of individual wafer-shaped elements without the need for sensors or initiators (for example light-barriers or the like). Finally a full single picture or true picture of each wafer-shaped element which is useful for later image data processing can be obtained by the method. The detection or recognition of edges and/or transitions between the wafer-shaped elements is performed within a hardware-based image data processing unit, which can be embodied by a programmable integrated circuit, in particular by a FPGA (Field Programmable Gate Array). Thus the method can be performed very rapidly and without using a PC-processor. In the prior art the occurring high processor load of common PC-based solutions normally leads to limitation of the speed of inspection and transport. A specific advantage of the invention is that considerably more wafers can be inspected than with PC-based solutions.

Preferably the method of the invention is performed by a line-scan camera which is continuously taking image data line-by-line and transverse to the movement direction of the conveyor belt, wherein edge detection is performed consecutively. This can be performed within a series of several sequenced lines, e.g. within a window of 200 lines. The detection of white/black transition indicates an edge at the beginning of a wafer-shaped element, e.g. of the particular solar cell or wafer. The detected edge indicates the beginning or start of each wafer and triggers the generation of a respective still picture. For generating the still pictures the subsequent image data, for example at least the subsequent 3450 lines, are used in order to represent the core portion or the kernel of the wafer-shaped element (e.g. of the wafer or solar cell).

In a preferred embodiment of the invention digital image photographs of the sequenced wafer-shaped elements are taken line-by-line, wherein the number of lines to be scanned is greater than a pre-defined number which represents an average size or a maximum size of a single wafer-shaped element. The number of lines taken for each photograph may comprise the pre-defined number plus at least one additional number which represents an overlapping area at the end of an individual wafer-shaped element. This means that a subsequent number of lines is also taken for representing an overlapping area at the end of each single wafer-shaped element. Thus the digital image data always fully covers the full size of the single wafer-shaped element (e.g. wafer), even when the size of the wafers varies due to production process or the speed of the conveyor belt alters.

In addition to this also a preceding number of lines representing an overlapping area at the beginning of each single wafer-shaped element can further be scanned. Thus a larger frame is defined which extends from at both ends of the core area of the wafer.

In a preferred embodiment the generation of the still picture is triggered at each detected edge by a control signal (trigger signal) which represents the indication of the beginning of the wafer-shaped element. Then the subsequent detected image data are used according to a pre-defined number of lines for generating at least the core area of the still picture. Preferably a pre-defined number of lines behind the core area is also scanned for generating a supplementary area of the still picture. if some of the sequenced wafers are too close to each other that no edge can be detected, the generation of the still picture is triggered by a synthetic control signal or trigger which represents a virtual indication of the beginning of the wafer-shaped element within the particular still picture. In any case, each trigger (normal or synthetic) starts a scan of a pre-defined number of lines for the generation of the still picture.

Again boundary areas or transition areas may also be detected before the assumed beginning and after the assumed end of the wafer. Thus the generated still picture may also comprise the region of transition to the preceding or succeeding wafer. The added boundary area at the beginning may comprise 200 lines. The boundary area at the end may comprise 800 lines and therefore may constitute a buffer area to compensate variation of the wafer size.

The method is preferably implemented in a programmable integrated circuit such as an FPGA (Field Programmable Gate Array). Thus a computer intensive embodiment of the invention comprising a PC computer unit or the like is superfluous.

These and further advantages also result from the subclaims.

The invention particularly comprises the advantage that the detection and generation of still pictures can be achieved without the use of complex sensor-technology or components such as light-barriers. Thus not only the costs for equipment acquisition are omitted but also the effort for calibration and re-adjustment of these components. The invention shall be applied particularly to the production of solar cells but shall not be limited to this, since it can also be used for each production process wherein a single element shall be identified or detected throughout a series of sequenced elements on a conveyor belt or the like.

BRIEF DESCRIPTION OF THE DRAWINGS

The invention and advantages resulting there from will be made more apparent from the following described embodiments with reference to the accompanying figures, in which.

DESCRIPTION OF THE PREFERRED EMBODIMENTS

Figure 1A:
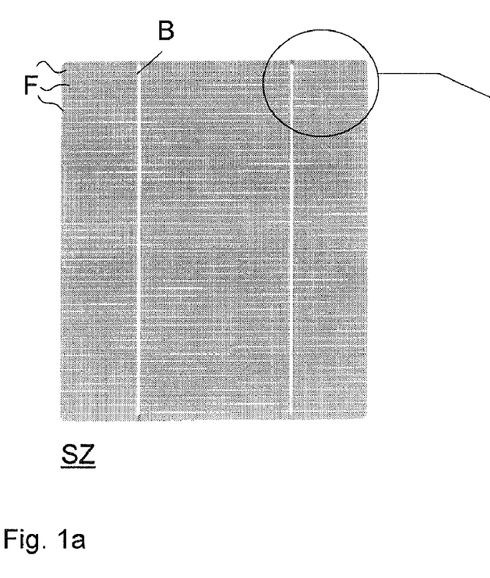
FIG. 1a/b illustrates an initial situation of the invention in which a single solar cell or a detail thereof is shown.
Figure 1B:
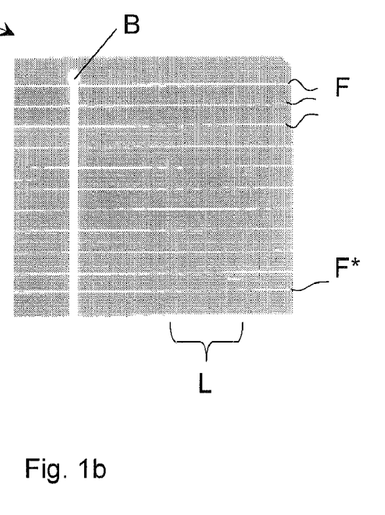

As shown in the schematic drawings of FIGS. 1a and 1b the produced solar cells SZ are for example rectangular-shaped wafers having each the size of 5×5 inch. Each wafer comprises a plurality of transverse so-called fingers F which represent semiconductor contact pathways. Crosswise thereto there are arranged two so-called bars B which represent the contact pathways or connecting conduits. It is the aim of an optical quality inspection to reliably detect imperfections or defective areas on the surface of each solar cell during the production process in order to sort out erroneous solar cells.

As FIG. 1b shows in more detail, single fingers can have failures by comprising for example interruptions. As an example of this a finger F* is shown in FIG. 1b, the finger having an interruption or a defect with the length of L. In order to get each solar cell under an optical inspection, the single solar cell first must be identified in the series of solar cells arranged in succession on the conveyor band.

Figure 2:
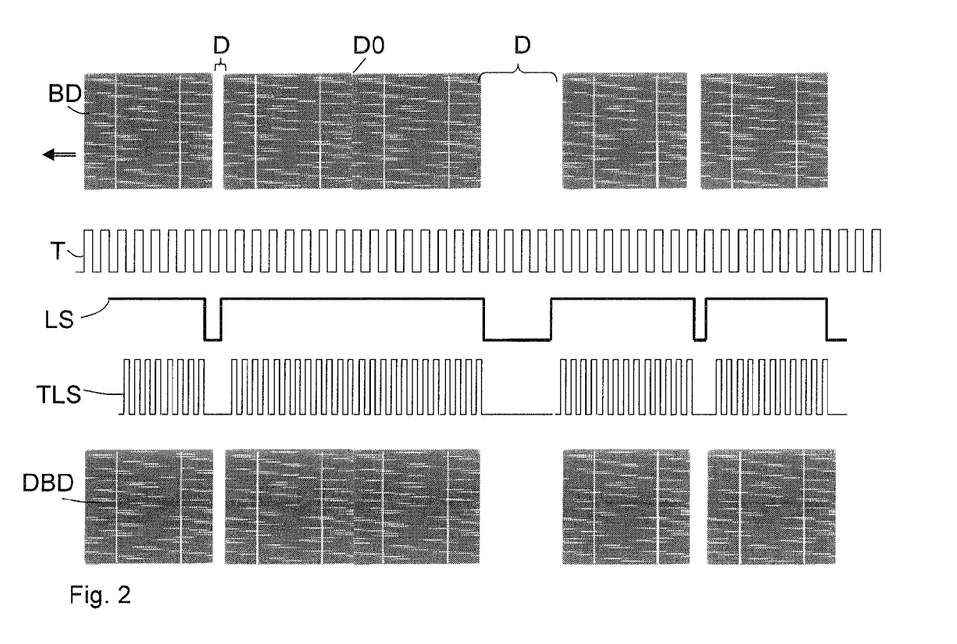
FIG. 2 illustrates a known method for generating still pictures by edge detection with the help of a sensor trigger, for example a light-barrier trigger.
Figure 3:
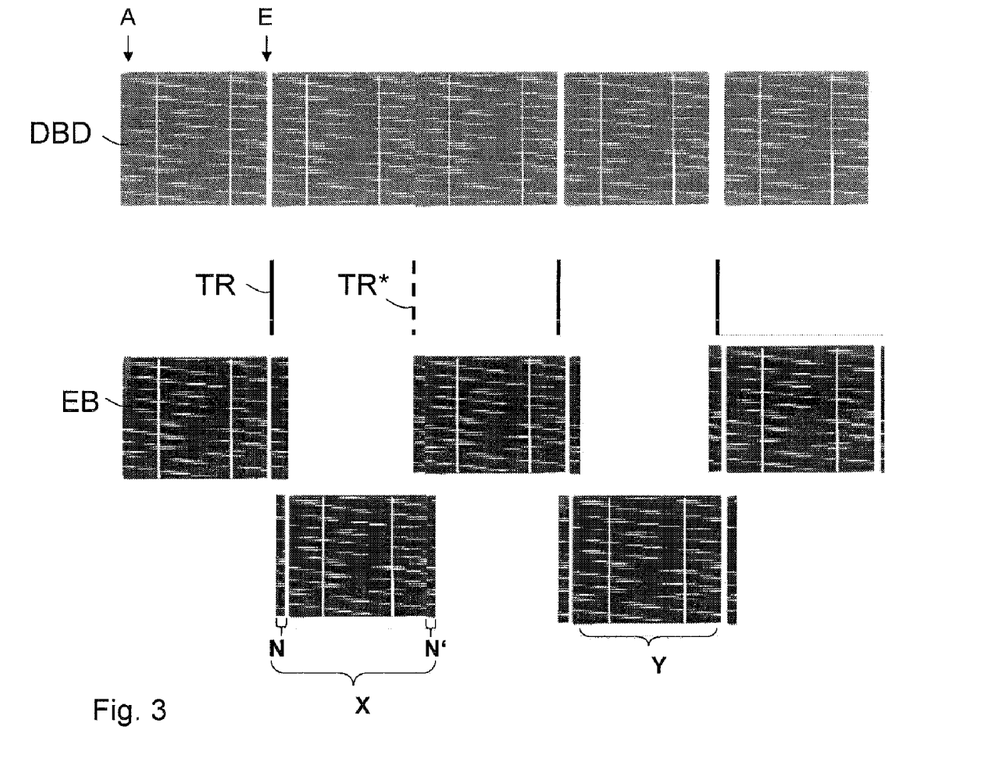
FIG. 3 illustrates the generation of still pictures of solar cells using the method according to the invention.

FIG. 2 illustrates a prior art method wherein by means of a sensor, such as a light-barrier, the beginning A or the end E of each wafer is detected (also see FIG. 3). FIG. 2 further illustrates the situation that the single solar cells SZ are arranged to each other very closely on the conveyor band BD. Normally some gaps D remain between the wafers which can easily be detected. However, it occurs quite often that two or more sequenced wafers or solar cells SZ are arranged so closely to each other that no detectable gap remains. in such cases the common detection by means of sensors fails. In the other part of FIG. 2 a snapshot of such a situation is shown wherein no optical detectable gap remains between the second and the third solar cells.

For the purpose of optical quality inspection the solar cells SZ are being moved on a conveyor band BD and are detected by a line-scan camera CAM (also see FIG. 5) which is controlled by a feeder rate clock T. Under good conditions and by means of a sensor, such as a light-barrier, each detectable gap or distance D can be identified and can be indicated in form of a sensor trigger LS. This sensor or light-barrier trigger LS may then be synchronized with the feeder rate clock T such that a signal TLS results. This signal TLS represents blockwise sections which each comprise several sequenced lines which therefore represent as single solar cell SZ.

If, however, under bad conditions the sensor cannot detect a gap, the corresponding sensor trigger LS therefore is not set and the signal TLS cannot help to distinguish between the single solar cells. Nevertheless it is possible to get a digital representation of the whole conveyor band BD by means of the detected image data in form of a digital overall picture DBD which is here referred to as "digitalized conveyor band". However, the extraction of still pictures is hindered or even impossible if transitions occur, which are all but without gaps, i.e. not showing any detectable distance between the wafers.

The method according to invention here finds a remedy in that the control for generating still pictures is performed by means of an edge detection which is executed on the basis of a hardware-based image processing of image data which are obtained by scanning step-by-step or even line-by-line. Preferably the generation of still pictures is triggered by control signal derived from the edge detection. For example a trigger is generated at each beginning A of a wafer, i.e. when a white/black transition is detected (also see FIG. 3). Then a pre-defined number of subsequent lines is scanned for generating the image data of the particular wafer. Further to this the invention also proposes to generate a synthetic trigger, if no edge can be detected at the present wafer. In this case the edge, which was detected before, is taken to mark the beginning of the preceding wafer. And by adding a pre-determined number of lines which comprise at least the average size or length of a single wafer the synthetic trigger is set to mark the virtual beginning of the present wafer and thus the start of the scan for this wafer.

Figure 4:
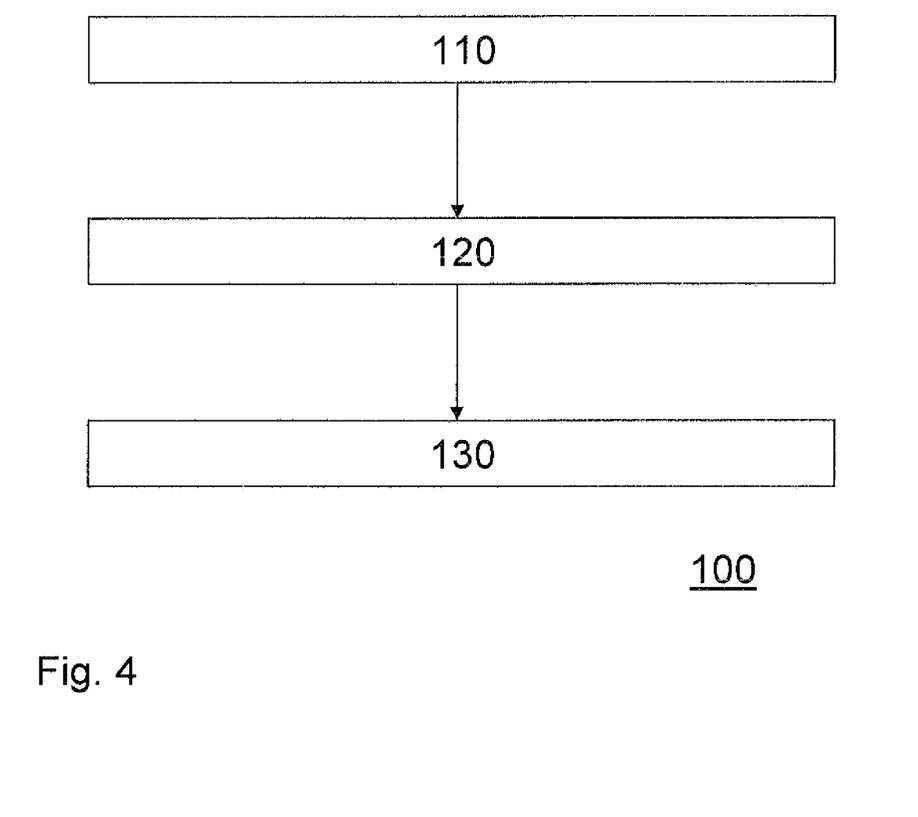
FIG. 4 is a flowchart illustrating the method according to the invention.

FIGS. 3 and 4 illustrate the principle of the invention by means of a first embodiment as follows:

For the method according to invention it is preferably assumed that the conveyor belt DB is periodically detected line-by-line and is at least partially stored in a buffer memory in form of a digital representation that is here referred to as "digitalized band" DBD. By analyzing these buffered image data it can be detected whether there are transitions between several sequenced lines in form of black/white or white/black transitions. For example a white/black transition indicates an edge KA at the beginning of a wafer (also see FIG. 5). If this is the case, the trigger signal TR is set. Thus a white/black transition and the corresponding trigger always indicate the beginning of the particular still picture.

If, however, no edge can be detected a synthetic trigger TR* is set at least after a predetermined number of Y lines have been passed. For example this number Y is 3450 and defines the corresponding average length of each wafer. Thus a synthetic trigger TR* can be generated, if no normal trigger can be set. Therefore a trigger signal TR or TR* is produced for each still picture EB in every case.

Each trigger controls the generation of corresponding still pictures EB in that the 3450 lines or the corresponding image data succeeding the trigger TR or TR* are interpreted to be the core area of the still picture EB. This core area (see Y in FIG. 3) is assumed to represent the true image of the respective solar cell within the generated still picture EB.

In addition to this transition overlapping areas beyond those edges are also detected or generated in that also the image data of the preceding lines and of the succeeding lines are recorded. For example also the N lines before each trigger TR or TR* are recorded for the generation of the still picture, wherein N is 200, as an example. Further to this also the N' following lines are recorded, wherein N' is for example 750. Thus always an overlapping area of at least 200 lines between adjacent still pictures is recorded.

In FIG. 3 a sequence of the generated still pictures is shown in a de-multiplexed or de-interleaved way in order to better illustrate also the resulting overlapping areas. In total the still picture EB comprises a number of X=4200 lines. Each still picture comprises the generated or reconstructed digital single photograph of the wafer including the mentioned edges and can therefore be used very well for a later image data processing, for example, in a PC.

With the help of FIG. 4 the method 100 according to invention is further illustrated in its process details:

In a first step 110 the image data of solar cells being arranged on the conveyor band is detected line-by-line. Then, in a step 120 edge detection is executed in order to detect the beginning of each solar cell. In a subsequent step 130 the still pictures are then generated under control of a trigger signal which is generated on the basis of the detected beginning of the solar cell.

Figure 5:
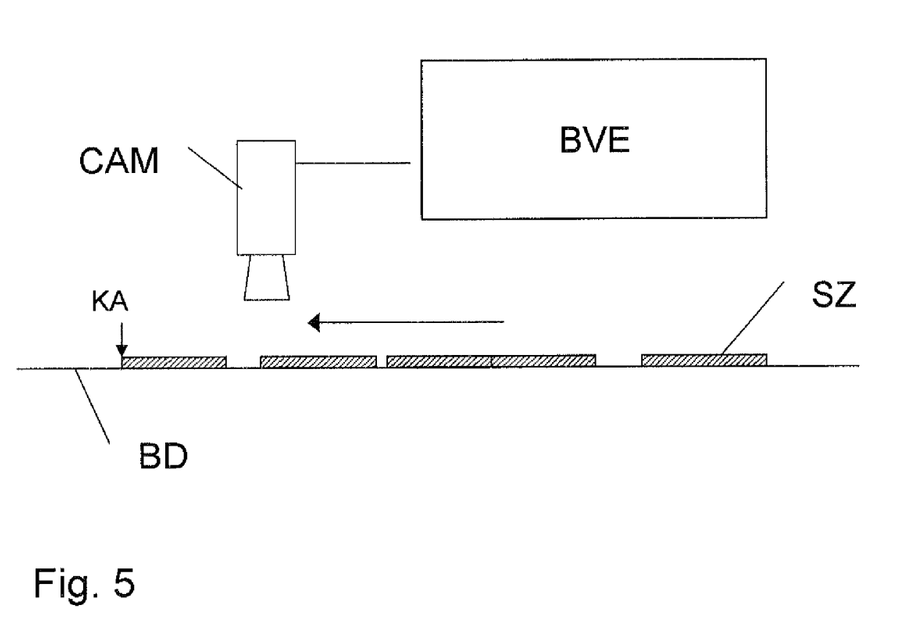
FIG. 5 is a block diagram of a device according to the invention.

Reference is also made to FIG. 5 showing the design of a device for performing the method. The device comprises a camera CAM for scanning the wafers SZ which are transported on the conveyor belt BD. The device further comprises a hardware-based image data processing unit BVE connected to the camera CAM. The hardware-based image data processing can preferably be implemented in the unit BVE which may be a programmable implemented circuit, such as a FPGA, so that an embodiment comprising a computer unit or PC can be omitted. The method is particularly used for inspection of the electro plating on the upper surface of the solar cell, in which an inspection of the contact fingers for default spots is performed. The production process is performed in a continuous flow with a belt speed of some meters per minute. The size of the wafers may be 5×5 inch or 125× 125 mm, wherein 48 fingers are inspected on each solar cell.

With the help of the proposed method the beginning of each wafer is clearly detected. In case of a missing gap or slot a synthetic trigger are automatically generated. The obtained still pictures thus also comprise areas of transition towards the preceding or succeeding solar cells. For the edge detection as such there are for example 32 following lines to be inspected in order to find out whether there is a white/black transition representing the beginning of a wafer. If this is the case the trigger is set. If no gap can be detected, then at least after 3450 further lines a synthetic trigger is set. Thus, a reliable control for generation of the still pictures is always achieved.

The hardware-based image data processing unit can be designed as a separate component module embodied outside of a PC or inside of a PC, e.g. on a plug-in card.

By outsourcing of the image data processing and the control into a FPGA, the possible speed of inspection and therefore the maximum production speed is increased. The necessary installation space within the production equipment is smaller since no bulky sensors are necessary. Because no light-barrier is needed anymore also the bulky and interference-prone adjustment of the distance between light-barrier and optical lens of the camera can be omitted. Because a line-scan camera is used here, the camera only needs to have a small slot sized access to view on the production belt. The inspection arrangement based on the invention is easier to be implemented, is easy to maintain and more powerful than common solutions.

Figure 6:
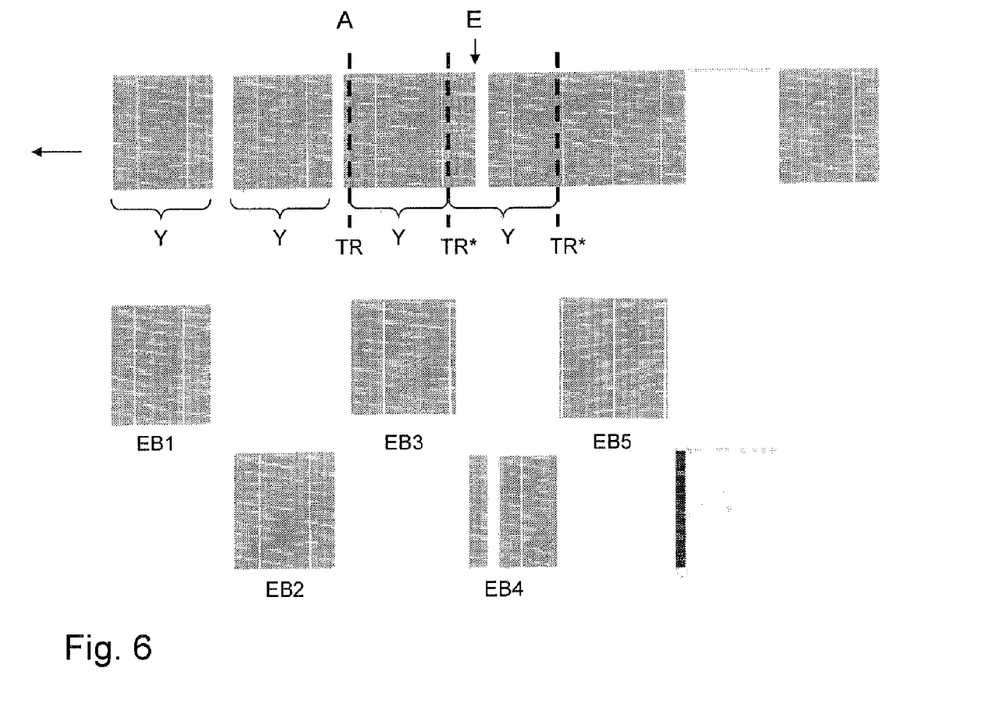
FIG. 6 illustrates the generation of still pictures of solar cells by image scanning without using overlapping areas.

The following description refers to another embodiment of the invention:

FIG. 6 illustrates the generation of still pictures of solar cells by image scanning without using overlapping areas. What can be seen there is that at the beginning of each wafer the camera starts to scan Y lines which represent the average length of a wafer. If no variation in the length of the wafers or speed of the conveyor belt occurs, useful still pictures representing the full size of a wafer, such as pictures EB1 or EB2, are produced. If however the lengths of the wafers differ and some are too large, such as shown by the third wafer on the belt, the scan results in a bad picture EB3 which does not cover the full size of said wafer. A further problem may occur, if some wafers are arranged very close to each other, such as the shown by the third and fourth wafers. In this case no edge (white/black transition) can be detected and thus no normal trigger can be set.

It then helps to generate a synthetic or artificial trigger TR* which would indicate the beginning of the subsequent wafer. This works well if all wafers would not be longer than Y lines or if the speed of the belt would not get too slow so that Y lines always cover a full size of a single wafer. In the example as shown in FIG. 6 the third wafer is, however, too long and thus the synthetic trigger TR* is generated too early. Consequently the subsequent picture EB4 does not fully cover the fourth wafer, but is shifted towards the preceding wafer which is the third wafer here.

Figure 7:
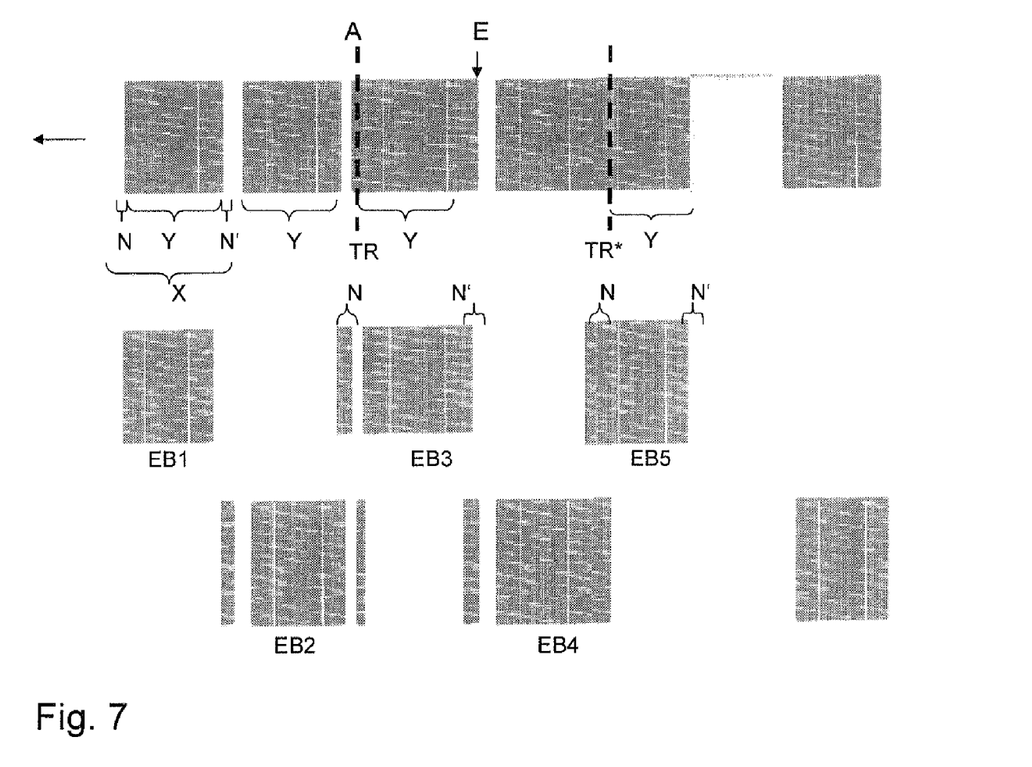
FIG. 7 illustrates the generation of still pictures of solar cells by image scanning with additionally overlapping areas.

Further to this, it can become even worse if the next trigger is also generated synthetically by just waiting Y lines after the first trigger TR* and then setting the next synthetic trigger TR*. This would lead to a further shift of the next produced picture EB5 and so forth. The setting of synthetic triggers TR* only works well, if all wafers are not larger than the Y lines. Thus it is helpful in many cases to define the number Y larger so that it covers the maximum size of wafers allowed due to the tolerance of the production process. However, the following description shows a solution which is even better:

FIG. 7 refers to a further embodiment illustrating the generation of still pictures of wafers, wherein the wafers are optically scanned by using additional overlapping areas at both ends of each wafer. What can be seen here is that at each beginning or start which is found by an edge detection a normal trigger TR is set, whereas a synthetic trigger TR* is only set if no beginning can be detected (see gapless transition between the third and the fourth wafer).

In this embodiment of the invention it is proposed to always set a normal trigger TR, if the edge at the beginning of a wafer can be detected and then to scan at least Y lines covering the maximum length of a single wafer and further to scan N' lines at the end of said wafer. Thus each picture, such as EB1, EB2 etc., covers at least Y+N' lines which is e.g. 3450+800=4250 lines.

It may happen that the edge detection cannot be performed precisely. Therefore it is proposed to also cover a preceding number of lines, namely number N, which is also added to enlarge each picture EB1, EB2 etc. around the fuzzy edge at the beginning of that wafer. This number N can comprise e.g. 200 lines. In total each picture, such as EB3, finally covers X'=N+Y+N' lines.

If no beginning of a wafer can be detected at all (see fourth wafer) a synthetic trigger TR* is set. It has to be understood that the trigger TR* just marks a virtual point of the beginning from which the real core area of Y lines is assumed to start. In order to make sure that each wafer is indeed fully covered by the respective picture there are more lines taken into account, namely also N' lines behind the Y lines and N lines before the starting point marked by TR*. In total each digital picture, such as EB5, then covers X'=Y+N+N' lines. The overlapping area at the end may have N'=800 lines and provides a data buffer to compensate the shift of pictures due to wafers differing in size or due to the belt speed altering. The overlapping area at the beginning may have N=200 lines and provides a data buffer to compensate unclear edge detection.

In summary the invention proposes to add further lines when scanning wafer-shaped elements and thus to generate enlarged pictures with more image data in order to compensate occurring variations in size and/or speed.

The invention may preferably be applied to image data processing of wafers within a solar cell production process, but is not limited thereto.

We claim:

1. A method of generating digital still pictures of wafer-shaped elements that are arranged in sequence on a conveyor belt within a production process, wherein the method comprises the steps of:
   a) taking the digital still pictures of the sequentially arranged wafer-shaped elements in sections step-by-step and transverse to a movement direction of the wafer-shaped elements on the conveyor belt and recording image data obtained thereby;
   b) evaluating the recorded image data by hardware-based image data processing to detect edges so as to indicate a beginning or an end of each of the wafer-shaped elements; and
   c) controlling the taking of the digital still pictures from detected image data according to the detected edges.

2. The method according to claim 1, wherein the digital still pictures of the sequentially arranged wafer-shaped elements are taken line-by-line and the number of lines taken for each of the digital still pictures is greater than a pre-defined number of lines representing an average size or a maximum size of an individual wafer-shaped element.

3. The method according to claim 2, wherein the number of lines taken for each of the digital still pictures comprises the pre-defined number plus at least one additional number representing an overlapping area at the beginning and/or at the end of each of said wafer-shaped elements.

4. The method according to claim 3, wherein the at least one additional number is a subsequent number of tines representing an overlapping area at the end of each of said wafer-shaped elements.

5. The method according to claim 3, wherein the at least one additional number is a preceding number of lines representing an overlapping area at the beginning of each of said wafer-shaped elements, and wherein the preceding number is different from a subsequent number of lines representing an overlapping area at the end of each of said wafer-shaped elements.

6. The method according to claim 2, wherein a predetermined number of lines is the number of lines taken for each of the digital still pictures and is greater than said pre-defined number representing said average size or said maximum size of said individual wafer-shaped element.

7. The method according to claim 2, wherein said pre-defined number of lines is that number of lines for generating at least a core-area of each of the digital still pictures.

8. The method according to claim 1, wherein the hardware-based image data processing is performed in a programmable integrated circuit.

9. The method according to claim 8, wherein the programmable integrated circuit is a field programmable gate array.

10. The method according to claim 1, wherein at each detected edge the generation of each of the digital still pictures is triggered by a respective control signal that indicates the beginning or the end of each of the wafer-shaped elements within each of the digital still pictures.

11. The method according to claim 10, wherein the respective control signal starts a scan of a corresponding pre-defined number of lines for generating each of the digital still pictures.

12. The method according to claim 1, wherein after each detected edge indicating the beginning, the subsequently detected image data are used according to a respective pre-defined number of sections, in particular to a respective pre-defined number of lines, for generating a core-area of each of the digital still pictures.

13. The method according to claim 12, wherein ahead and/or behind each detected edge according to the respective pre-defined number of sections, in particular according to the respective pre-defined number of lines, the image data detected therein are used for generating a supplementary area of each of the digital still pictures.

14. The method according to claim 1, wherein, when no edge of a wafer-shaped element is detected, the generation of each of the digital still pictures is triggered by a respective synthetic control signal that indicates the beginning or of the end of each of the wafer-shaped elements within each of the digital still pictures.

15. The method according to claim 14, wherein the respective synthetic control signal starts a scan of a corresponding pre-defined number of lines for generating a respective one of the digital still pictures.

16. The method according to claim 1, wherein the wafer-shaped elements are flat products or flat pre-products.

17. The method according to claim 16, wherein the flat products or flat pre-products are semi-conductor wafers.

18. The method according to claim 17, wherein the semi-conductor wafers are solar cells.

19. A device for generating digital still pictures of wafer-shaped elements, which are arranged sequentially on a conveyor belt and transported on the conveyor belt during a production process, said device comprising:

a camera that takes the digital still pictures of the sequenced wafer-shaped elements vertically in sections step-by-step and transverse to the motion direction of the wafer-shaped elements and that records image data obtained thereby; and a hardware-based image data processing unit for detecting edges by data evaluation of the image data that indicates a beginning or of an end of each of the wafer-shaped elements and for controlling generation of the digital still pictures from the detected image data according to the detected edges.

20. The device as defined in claim 19, wherein the camera is a line-scan camera that takes the digital still pictures of the sequentially arranged wafer-shaped elements line-by-line and that scans a number of lines for each of the digital still pictures which is greater than a pre-defined number representing an average size or maximum size of an individual wafer-shaped element.

21. The device as defined in claim 19, wherein the hardware-based image data processing unit is a programmable integrated circuit.

22. The device according to claim 21, wherein the programmable integrated circuit is a field programmable gate array.

* * * * *